United States Patent
Goto et al.

(10) Patent No.: US 11,471,574 B2
(45) Date of Patent: Oct. 18, 2022

(54) BLOOD-PURIFICATION-TREATMENT SUPPORT SYSTEM

(71) Applicant: Nikkiso Company Limited, Tokyo (JP)

(72) Inventors: Hitoshi Goto, Shizuoka (JP); Kunihiko Akita, Shizuoka (JP); Masahiro Toyoda, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 140 days.

(21) Appl. No.: 16/398,490

(22) Filed: Apr. 30, 2019

(65) Prior Publication Data

US 2019/0255239 A1 Aug. 22, 2019

Related U.S. Application Data

(63) Continuation of application No. PCT/JP2017/040552, filed on Nov. 10, 2017.

(30) Foreign Application Priority Data

Nov. 11, 2016 (JP) .............................. JP2016-220799

(51) Int. Cl.
*A61M 1/16* (2006.01)
*A61B 5/02* (2006.01)
(Continued)

(52) U.S. Cl.
CPC ............. *A61M 1/1601* (2014.02); *A61B 5/00* (2013.01); *A61B 5/02* (2013.01); *A61B 5/22* (2013.01);
(Continued)

(58) Field of Classification Search
None
See application file for complete search history.

(56) References Cited

U.S. PATENT DOCUMENTS

2003/0011646 A1  1/2003  Levine et al.
2006/0289342 A1* 12/2006  Sugioka ............... A61M 1/1615
                                                        210/85
(Continued)

FOREIGN PATENT DOCUMENTS

EP    3 033 704 A1    6/2016
JP    H11-342198      12/1999
(Continued)

OTHER PUBLICATIONS

International Search Report PCT/JP2017/040552 dated Dec. 26, 2018, published as WO2018/088513A1.
(Continued)

*Primary Examiner* — Jonathan M Peo
(74) *Attorney, Agent, or Firm* — Young Basile Hanlon & MacFarlane, P.C.

(57) ABSTRACT

A blood-purification-treatment support system is capable of making an accurate judgement of whether or not any treatment conditions for blood purification treatment should be changed. The blood-purification-treatment support system is capable of supporting blood purification treatment. The system includes a storage device that stores patient-specific patient data that are acquired on a plurality of days including at least no-treatment days on which blood purification treatment is not conducted, an estimating device that compares the patient data for the plurality of days stored in the storage device with one another and estimates a pre-treatment patient state regarding blood purification treatment, and a judging device that judges from the pre-treatment patient state estimated by the estimating device whether or not any treatment conditions for blood purification treatment should be changed.

20 Claims, 13 Drawing Sheets

(51) Int. Cl.
    *A61B 5/22*     (2006.01)
    *A61B 5/00*     (2006.01)
    *A61M 1/14*     (2006.01)
    *G16H 10/60*     (2018.01)
    *A61B 5/01*     (2006.01)
    *A61B 5/145*     (2006.01)

(52) U.S. Cl.
    CPC ............... *A61M 1/14* (2013.01); *A61B 5/01* (2013.01); *A61B 5/14535* (2013.01); *A61B 5/4842* (2013.01); *G16H 10/60* (2018.01)

(56) References Cited

U.S. PATENT DOCUMENTS

| | | | | |
|---|---|---|---|---|
| 2010/0010428 A1* | 1/2010 | Yu | ......................... | A61M 1/282 604/29 |
| 2012/0273420 A1* | 11/2012 | Gerber | .................. | A61B 5/053 210/647 |
| 2013/0211206 A1* | 8/2013 | Sands | .................... | G16H 40/63 600/301 |
| 2013/0310726 A1* | 11/2013 | Miller | ................ | G06Q 30/0601 604/5.04 |

FOREIGN PATENT DOCUMENTS

| | | |
|---|---|---|
| JP | 2001-060230 | 3/2001 |
| JP | 2002-056099 | 2/2002 |
| JP | 2005-267364 A | 9/2005 |
| JP | 2006-285488 | 10/2006 |
| JP | 2014-217528 | 11/2014 |
| WO | 2018/088513 | 5/2018 |

OTHER PUBLICATIONS

European Search Report dated May 4, 2020 for corresponding European Patent Application No. 17 868 687.9.

\* cited by examiner

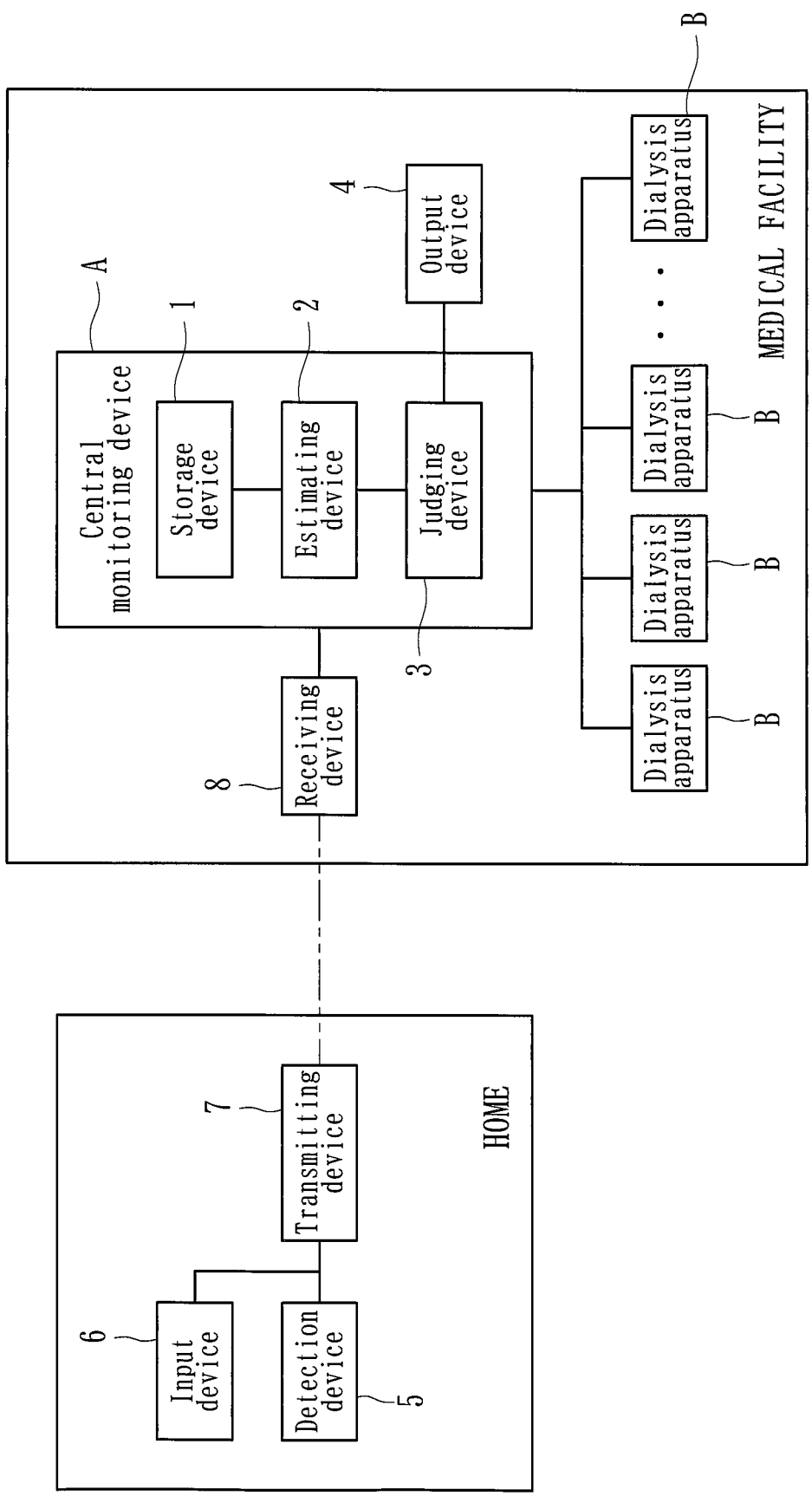
[Fig. 1]

[Fig. 2]
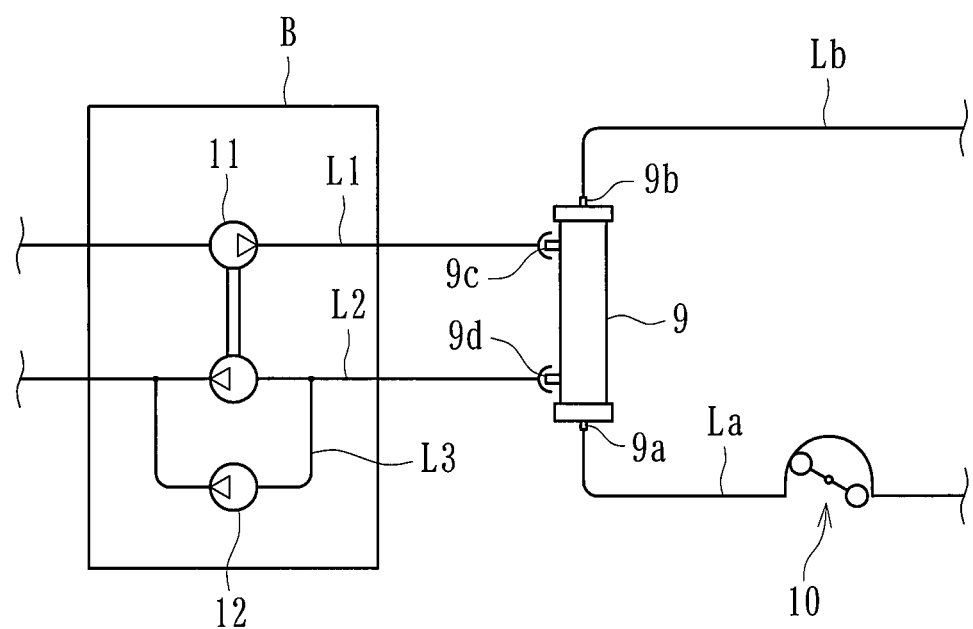

[ Fig. 3-1 ]

| Measurement parameter | | Measuring device | | | | | | Major dialysis conditions etc. to be changed |
|---|---|---|---|---|---|---|---|---|
| | | Treatment device | Testing device | Monitoring device | Home medical device | Wearable terminal | Health care device | |
| Noninvasive blood pressure | | ○ | ○ | ○ | ○ | ○ | | Ultrafiltration rate |
| Heart rate | | ○ | ○ | ○ | ○ | ○ | | Ultrafiltration rate |
| Pulse rate | | ○ | ○ | ○ | ○ | ○ | ○ | Ultrafiltration rate |
| SpO₂ | | | ○ | ○ | | ○ | | Ultrafiltration volume, dialysis time |
| Body temperature | | ○ | ○ | ○ | ○ | ○ | | Dialysate temperature |
| Respiration | | ○ | ○ | ○ | | | | Ultrafiltration volume, dialysis time |
| Urine | Urinary protein | | ○ | | ○ | | | |
| | Urinary sugar | | ○ | | ○ | | | |
| | Urine occult blood | | ○ | | | | | |
| | Urinary sediment | | ○ | | | | | |
| | Urinary specific gravity | | ○ | | | | | |
| | pH | | ○ | | | | | Dialysate comporition |
| Blood | Liver-related test | Total protein | | ○ | | | | | Dialyzer |
| | | Albumin | | ○ | | | | | Dialyzer |
| | | AST (GOT) | | ○ | | | | | |
| | | ALT (GPT) | | ○ | | | | | |
| | | γ-GTP | | ○ | | | | | |
| | Kidney-related test | Creatinine (Cr) | | ○ | | | | | Dialyzer |
| | Uric acid (UA) | | ○ | | | | | |
| | Lipid-related test | Total cholesterol (TC) | | ○ | | | | | |
| | | HDL cholesterol | | ○ | | | | | |
| | | LDL cholesterol | | ○ | | | | | |
| | | Neutral fat (TG) | | ○ | | | | | |
| | Glucose metabolism test | Blood sugar level (FPG) | | ○ | | | | | |
| | | HbA1C (NGSP) | | ○ | | | | | |
| | Blood-cell -related test | Red Blood cell (RBC) | | ○ | | | | | |
| | | Hemoglobin (Hb) | | ○ | | | | | |
| | | Hematocrit (Ht) | | ○ | | | | | Ultrafiltration rate |
| | | MCV | | ○ | | | | | |
| | | MCH | | ○ | | | | | |
| | | MCHC | | ○ | | | | | |
| | | White blood cell (WBC) | | ○ | | ○ | | | |
| | | Number of platelets (PLT) | | ○ | | | | | |
| | Infectious disease test | CRP | | ○ | | | | | Dialyzer |

[ Fig. 3-2 ]

| Measurement parameter | | Measuring device | | | | | | Major dialysis conditions etc. to be changed |
|---|---|---|---|---|---|---|---|---|
| | | Treatment device | Testing device | Monitoring device | Home medical device | Wearable terminal | Health care device | |
| Body composition | Body weight | | O | | O | | | Ultrafiltration volume, dialysis time |
| | Amount of water in body | | O | | | | | Ultrafiltration volume, dialysis time |
| | Amount of water in cell | | O | | | | | Ultrafiltration volume, dialysis time |
| | Weight without fat | | O | | | | | |
| | Muscle mass | | O | | | | | |
| | Amount of protein | | O | | | | | |
| | Amount of mineral | | O | | | | | |
| | Body cell mass | | O | | | | | |
| | Body fat mass | | O | | | | | |
| | Body fat rate | | O | | | | | |
| | Basal metabolic rate | | O | | | | | Ultrafiltration rate, blood flow rate |
| | ECW/TBW | | O | | O | | | |
| | BMI | | O | | | | | |
| | Impedance | | O | | | | | |
| Body measurement | Height | | O | | O | | | |
| | Abdominal circumference | | O | | O | | | |
| | Chest circumference | | O | | O | | | |
| Amount of activities | Number of paces | | | | | O | O | Ultrafiltration rate, blood flow rate, Dialysis time |
| | Walking distance | | | | | O | O | Ultrafiltration rate, blood flow rate, Dialysis time |
| | Hours of walking | | | | | O | O | Ultrafiltration rate, blood flow rate, Dialysis time |
| | Calorie consumption | | | | | O | O | Ultrafiltration rate, blood flow rate, Dialysis time |
| | Hours of sleep | | | | | O | O | |
| Behavior record | Meals — Calorie intake | | | | | | | Ultrafiltration rate, blood flow rate, Dialysis time |
| | Meals — Salt intake | | | | | | | Ultrafiltration volume, dialysis time |
| | Meals — Nutrient | | | | | | | Dialysate comporion, dialysate concentration |
| | Medication — Prescribed amount/dosage amount | | | | | | | |
| | Smoking — Quantity | | | | | | | |
| | Drinking — Quantity | | | | | | | |
| Data monitored by dialysis apparatus | Total blood volume — Ht | O | | | | | | Ultrafiltration rate |
| | Total blood volume — ΔBV | O | | | | | | Ultrafiltration rate |
| | Total blood volume — PRR | O | | | | | | Ultrafiltration rate |
| | Monitored dialysis rate — Kt/V | O | | | | | | Dialyzer |
| | Monitored dialysis rate — URR | O | | | | | | Dialyzer |

[ Fig. 4 ]
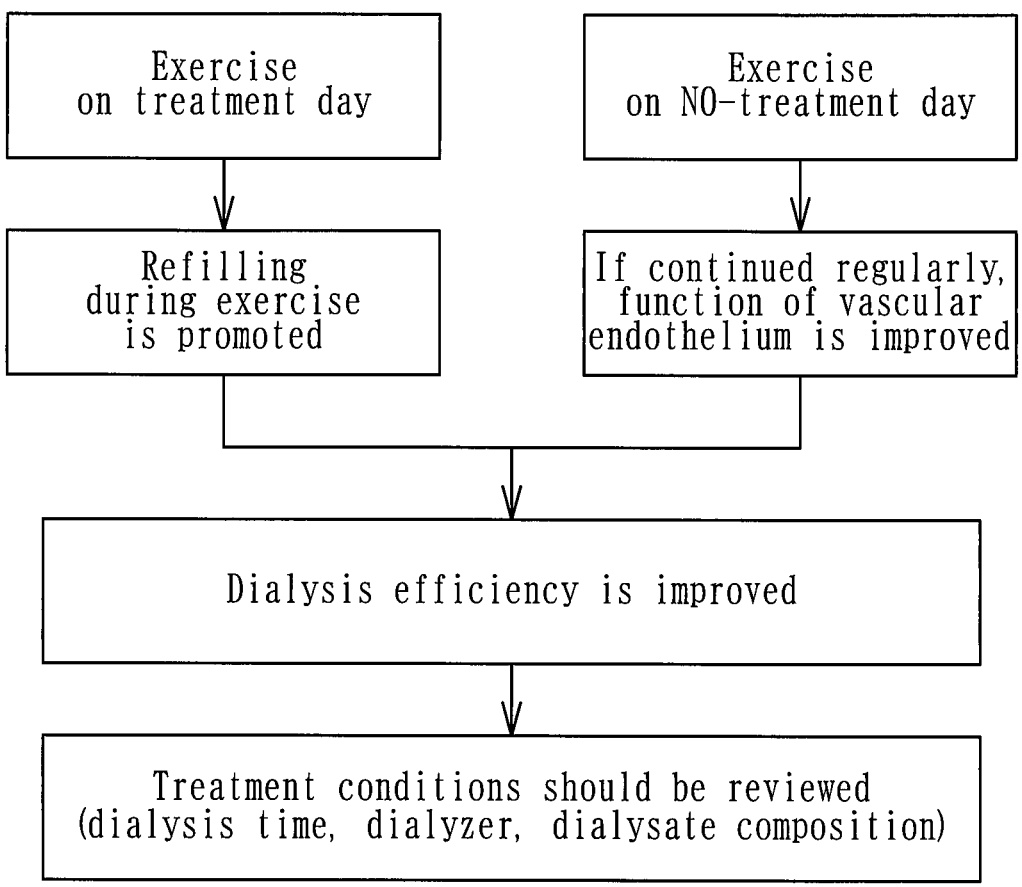

[ Fig. 5 ]
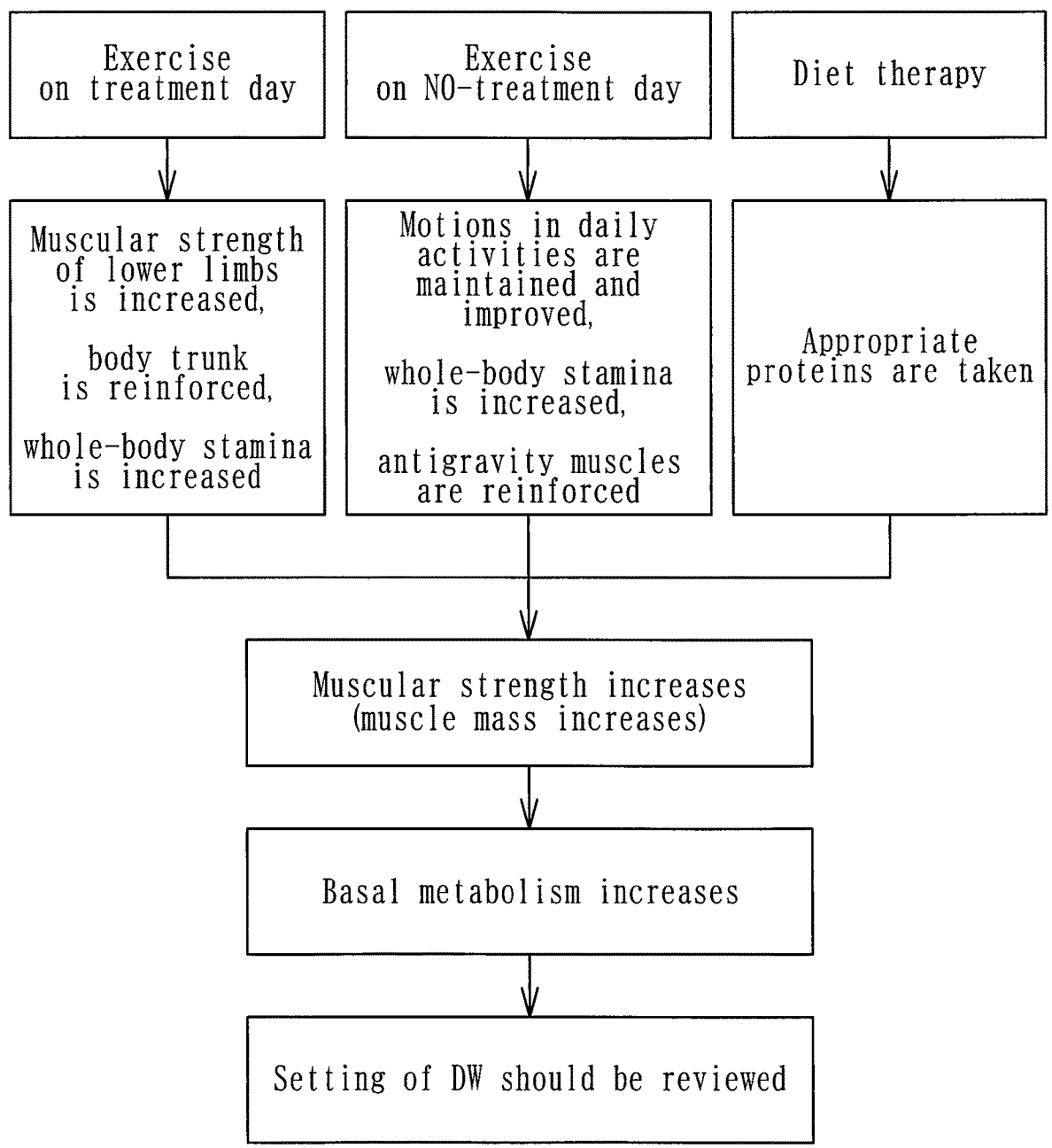

[Fig. 6]
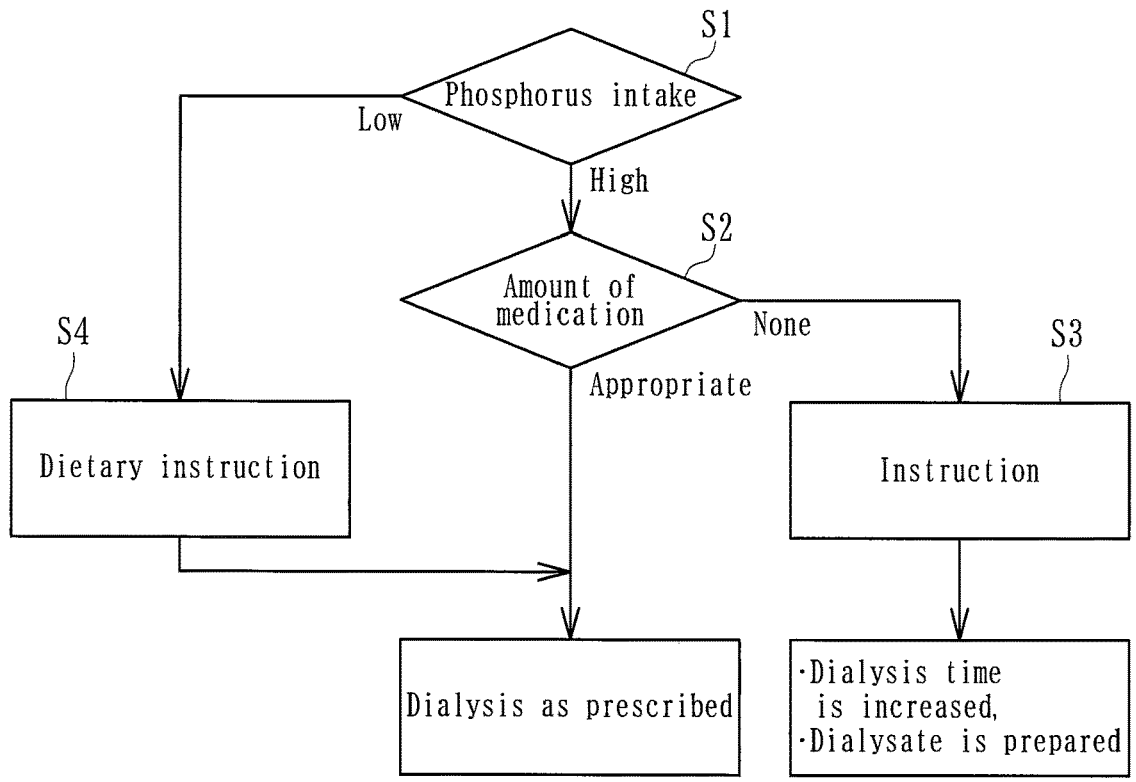
[Fig. 7]
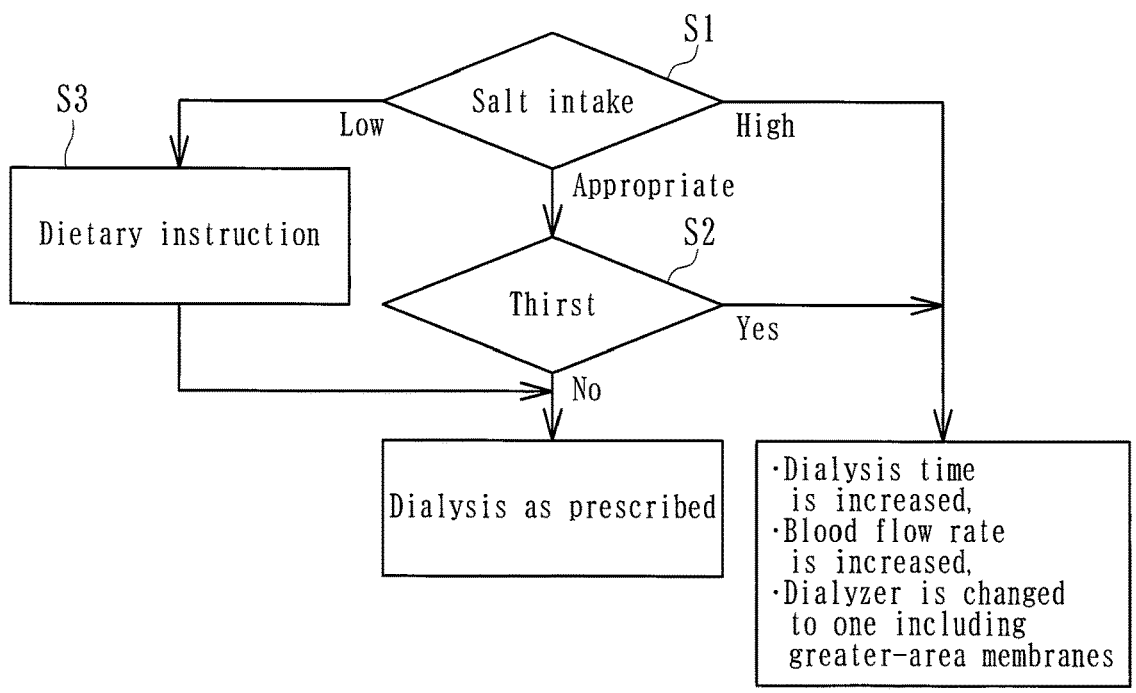

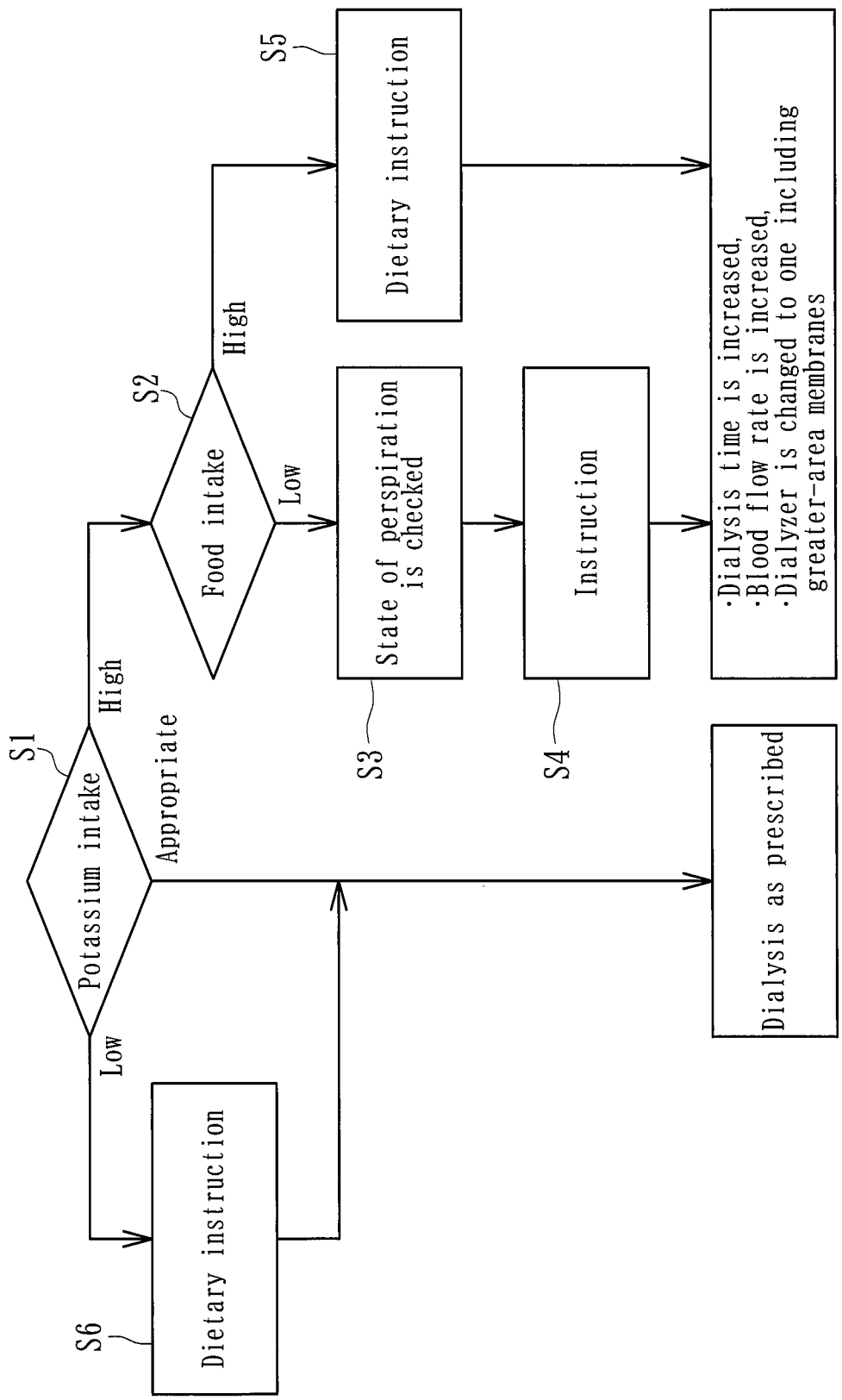
[ Fig. 8 ]

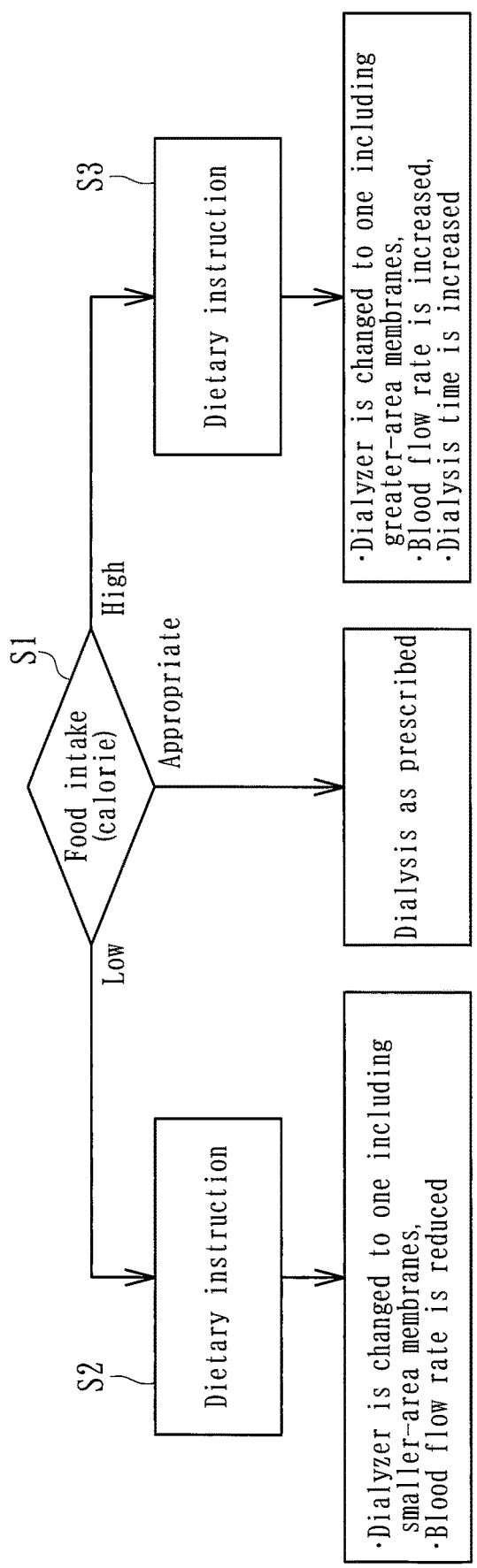
[ Fig. 9 ]

[Fig. 10]
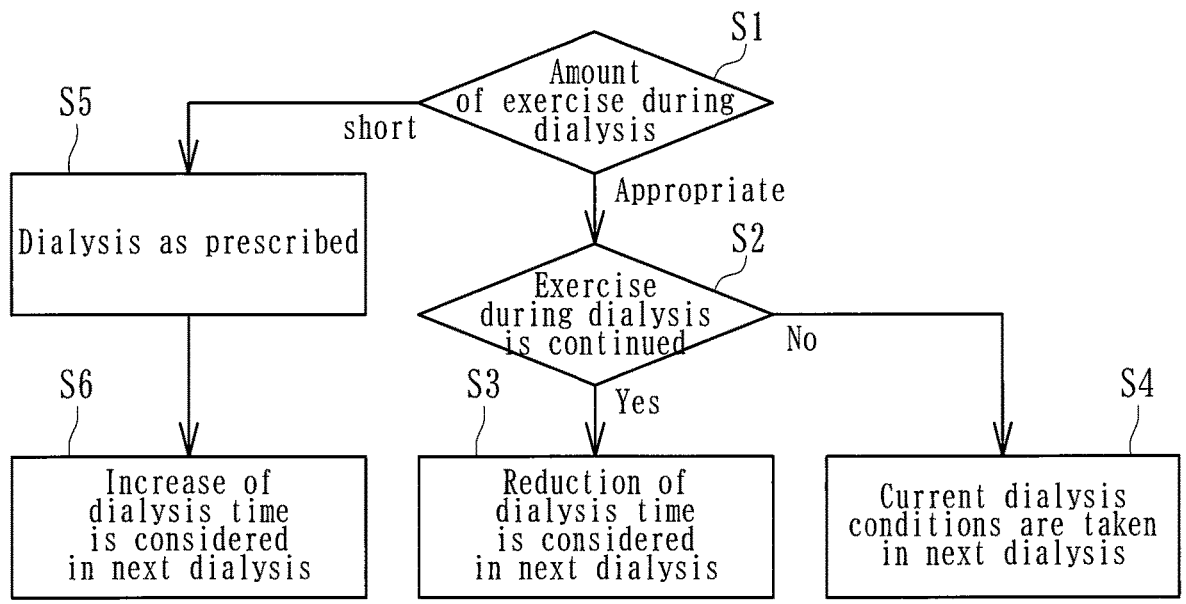
[Fig. 11]
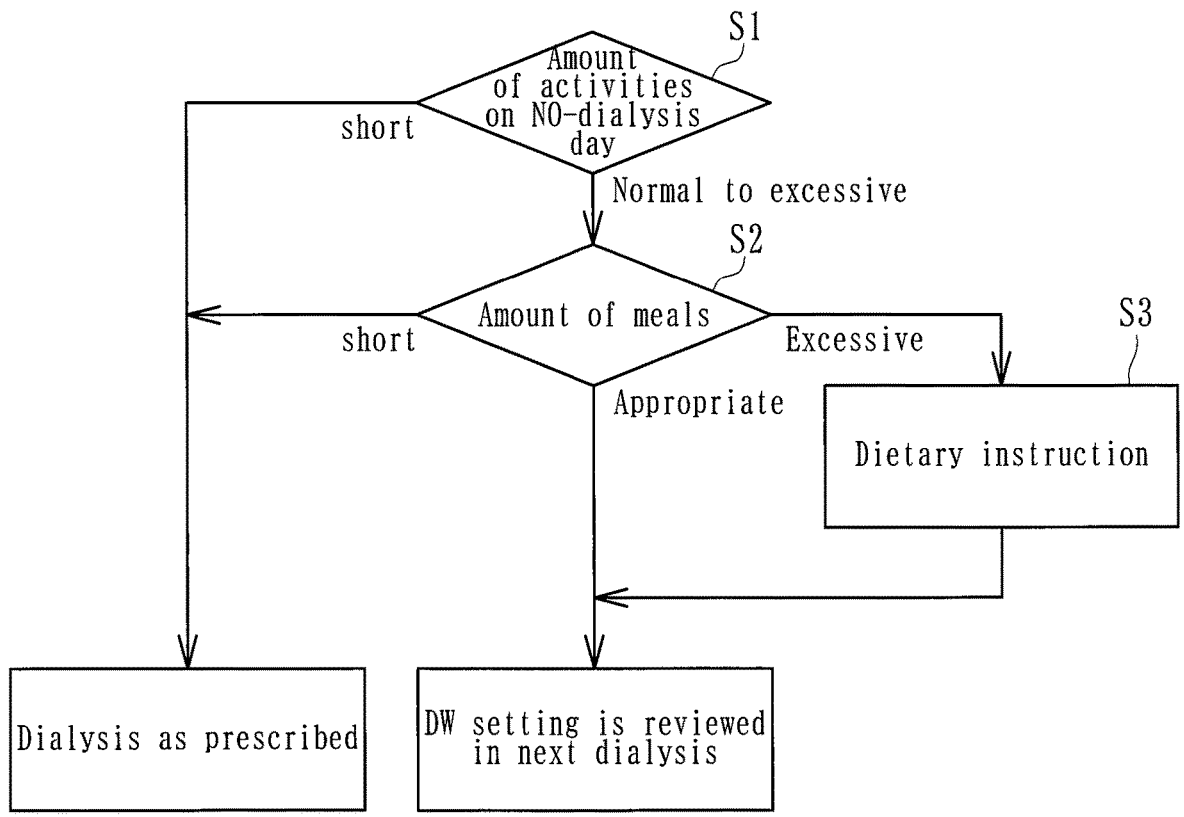

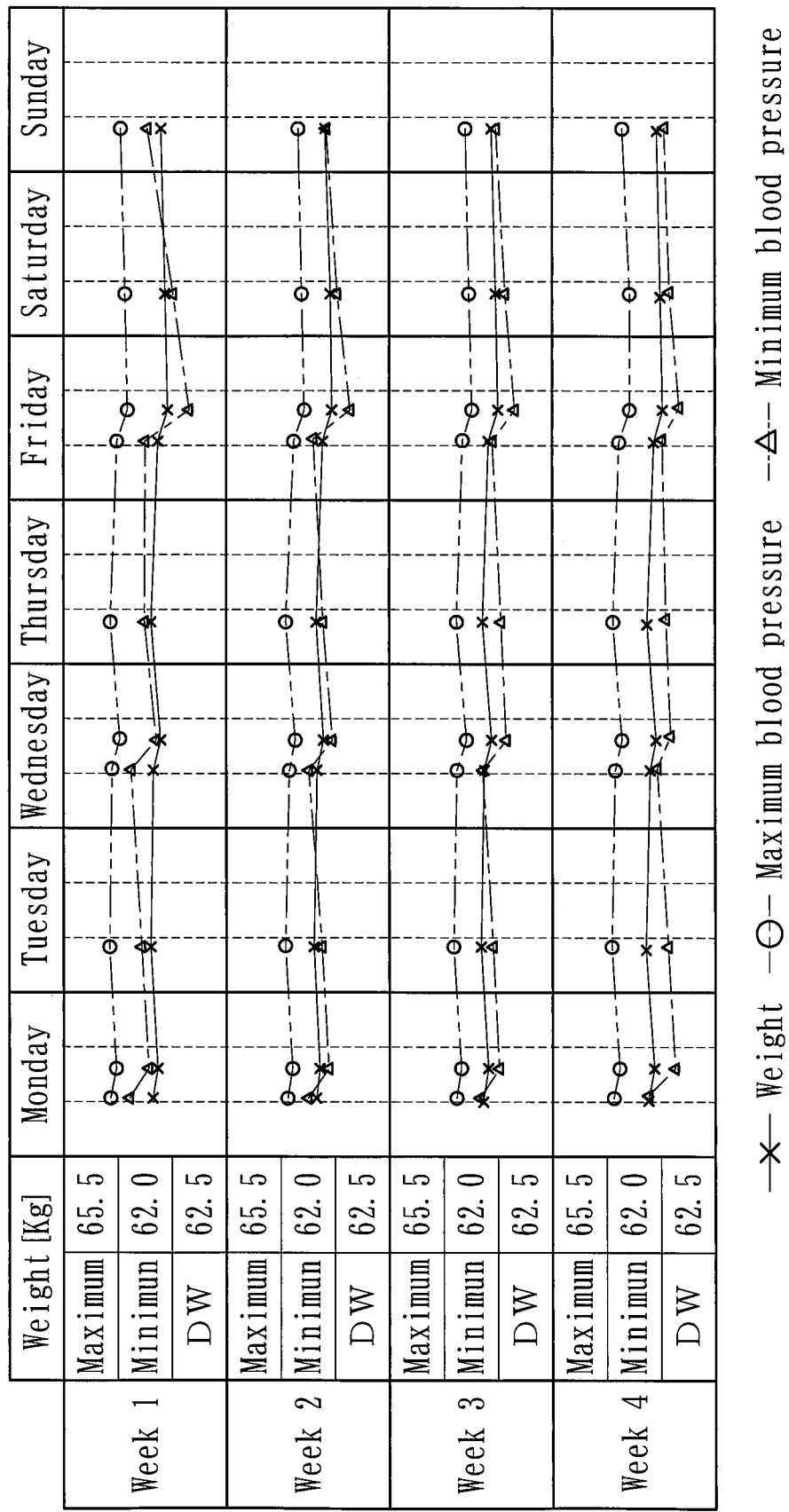
[ Fig. 12 ]

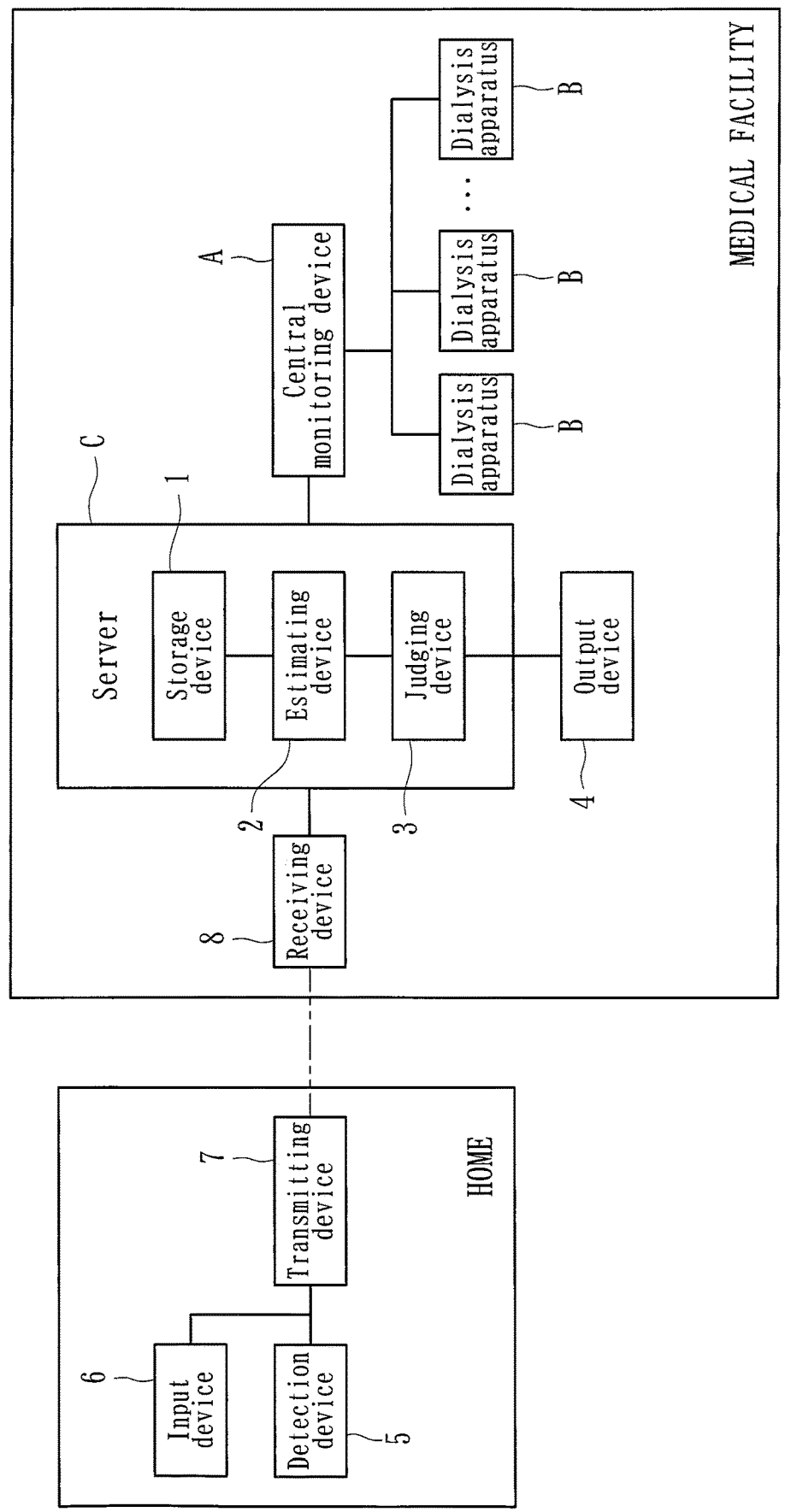
[ Fig. 13 ]

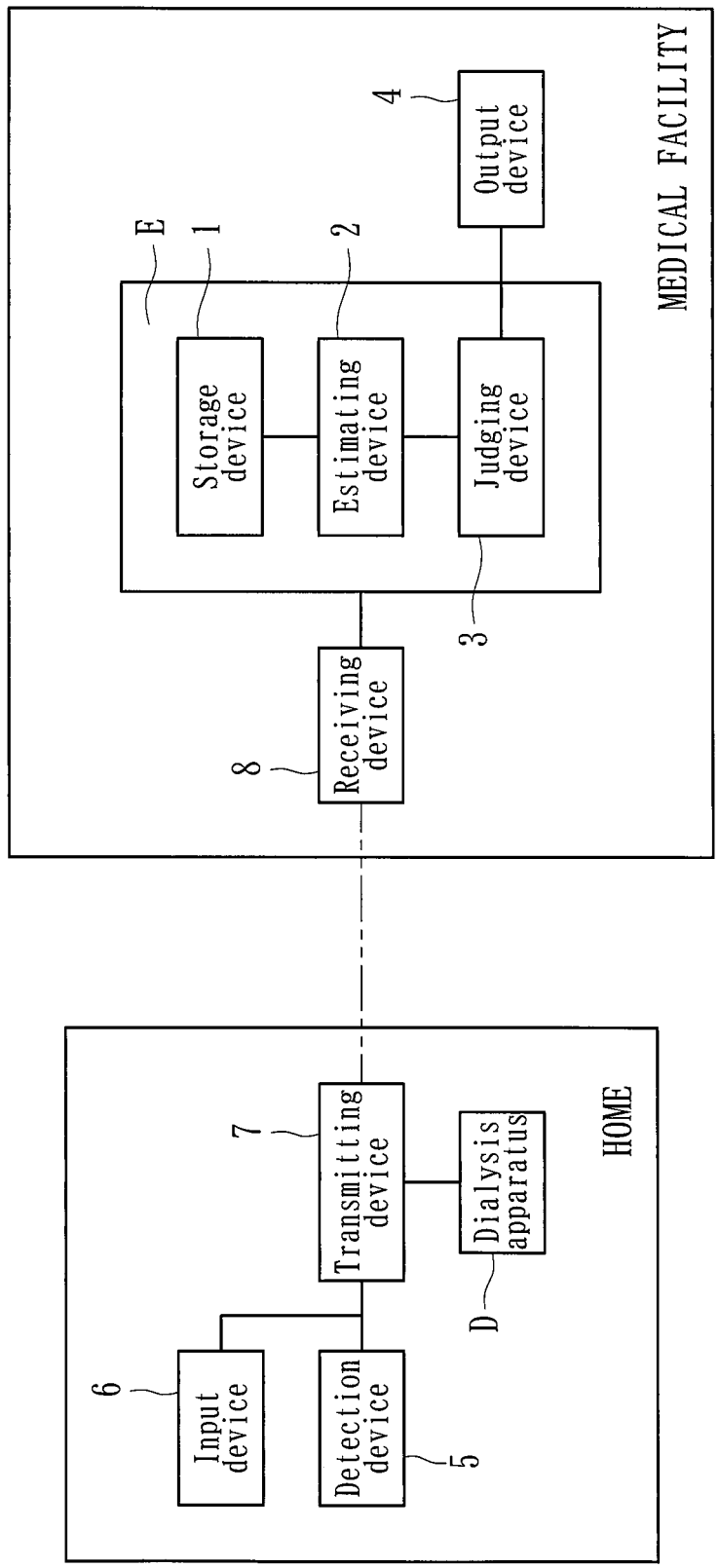
[ Fig. 14 ]

BLOOD-PURIFICATION-TREATMENT
SUPPORT SYSTEM

FIELD

The present invention relates to a blood-purification-treatment support system capable of supporting blood purification treatment.

BACKGROUND

Hemodialysis treatment (dialysis treatment) is one of several kinds of blood purification treatment. In hemodialysis treatment, blood of a patient is extracted and is put to extracorporeal circulation, in which unnecessary substances and excessive water are removed by a blood purification device, and the blood thus purified is returned to the body. Typically, hemodialysis treatment is conducted for about four hours every other day. Therefore, unnecessary substances accumulated in two days need to be removed in four hours. During such a treatment, the hemodynamics of the patient changes greatly.

Under such circumstances, pieces of information such as the progress of the treatment, the body weight to be controlled, the results of blood tests, and so forth during dialysis given to the dialysis patient need to be checked. Patient data regarding dialysis treatment, such as the progress of the treatment, the body weight, the results of blood tests, and so forth, acquired for the dialysis patient are stored in a server or the like provided in a medical facility such as a hospital, so that medical staff including doctors can refer to the patient data in conducting dialysis treatment. Hitherto, as disclosed by PTL 1 to 3 for example, some support systems have been proposed that each store patient data acquired in a treatment or in tests and output the patient data in a subsequent treatment, thereby supporting the setting of treatment conditions and so forth.

PTL 1: Japanese Unexamined Patent Application Publication No. 11-342198

PTL 2: Japanese Unexamined Patent Application Publication No. 2006-285488

PTL 3: Japanese Unexamined Patent Application Publication No. 2014-217528

SUMMARY OF INVENTION

In the above known techniques, however, patient data are acquired and stored only on days when the treatment or the tests are conducted. Hence, there has been a problem in that whether or not any treatment conditions should be changed can't be judged from daily patient data including those acquired on days when the treatment is not conducted. Specifically, if a treatment is conducted after several days from the day of the last treatment or test, patient data may change greatly from the data acquired in the last treatment or test. If whether or not any treatment conditions should be changed is judged from such patient data, the result of the judgement may be inappropriate.

The present invention has been conceived in view of the above circumstances and provides a blood-purification-treatment support system capable of making an accurate judgement of whether or not any treatment conditions for blood purification treatment should be changed.

DETAILED DESCRIPTION

According to the teachings herein, there is provided a blood-purification-treatment support system capable of supporting blood purification treatment, the system including a storage device that stores patient-specific patient data that are acquired on a plurality of days including at least no-treatment days on which blood purification treatment is not conducted, an estimating device that compares the patient data for the plurality of days stored in the storage device with one another and estimates a pre-treatment patient state regarding blood purification treatment, and a judging device that judges from the pre-treatment patient state estimated by the estimating device whether or not any treatment conditions for blood purification treatment should be changed.

According to the teachings herein, the blood-purification-treatment support system taught herein further includes an output device capable of outputting a result of a judgement made by the judging device.

According to the teachings herein, in the blood-purification-treatment support system taught herein, the patient data include patient's lifestyle data or a patient's vital parameter.

According to the teachings herein, in the blood-purification-treatment support system taught herein, the patient's lifestyle data include at least data regarding contents of meals or an amount of exercise taken by a patient.

According to the teachings herein, in the blood-purification-treatment support system taught herein, the patient's lifestyle data include medication data for a patient or a parameter regarding a sample collected from the patient.

According to the teachings herein, the blood-purification-treatment support system taught herein further includes a detection device capable of detecting the patient data acquired on the no-treatment days, and a transmitting device capable of transmitting to the storage device the patient data detected by the detection device or the patient data inputted by an operator.

According to the teachings herein, in the blood-purification-treatment support system taught herein, the detection device is a home medical device, a health care device, or a wearable terminal.

According to the teachings herein, in the blood-purification-treatment support system taught herein, the storage device is included either in a central monitoring device capable of transmitting a signal regarding blood purification treatment to a blood purification apparatus provided in a medical facility, or in a server capable of transmitting information on the patient to the central monitoring device; and the storage device is capable of storing not only the patient data but also patient data acquired by the blood purification apparatus during blood purification treatment.

According to the teachings herein, in the blood-purification-treatment support system taught herein, the patient data stored in the storage device are displayable in a time course.

According to the teachings herein, patient data acquired on a plurality of days including no-treatment days are stored, and the stored patient data for the plurality of days are compared with one another, whereby the pre-treatment patient state is estimated, and whether or not any treatment conditions for blood purification treatment should be changed is judged. Therefore, the judgement of whether or not any treatment conditions for blood purification treatment should be changed can be made accurately.

According to the teachings herein, the blood-purification-treatment support system includes the output device that is capable of outputting the result of the judgement made by the judging device. Therefore, medical staff including doctors can easily and assuredly grasp the result of the judgement made by the judging device.

According to the teachings herien, the patient data include patient's lifestyle data or a patient's vital parameter. Therefore, the pre-treatment patient state can be estimated assuredly, and the judgement of whether or not any treatment conditions for blood purification treatment should be changed can be made more accurately.

According to the teachings herein, the patient's lifestyle data include at least data regarding the contents of meals or the amount of exercise taken by the patient. Therefore, the patient state that has been affected by meals and exercise can be estimated assuredly, and the judgement of whether or not any treatment conditions for blood purification treatment should be changed can be made much more accurately.

According to the teachings herein, the patient's lifestyle data include medication data for that patient or a parameter regarding a sample collected from the patient. Therefore, the patient state can be estimated assuredly from the state of medication or the parameter regarding the sample, and the judgement of whether or not any treatment conditions for blood purification treatment should be changed can be made much more accurately.

According to the teachings herein, the blood-purification-treatment support system includes the detection device capable of detecting patient data acquired on no-treatment days, and the transmitting device capable of transmitting to the storage device the patient data detected by the detection device or the patient data inputted by an operator. Therefore, the patient data can be transmitted from a place separate from a medical facility.

According to the teachings herein, the detection device is a home medical device, a health care device, or a wearable terminal. Therefore, the patient data can be detected easily.

According to the teachings herein, the storage device is included either in the central monitoring device capable of transmitting a signal regarding blood purification treatment to a blood purification apparatus provided in a medical facility, or in the server capable of transmitting information on the patient to the central monitoring device. Furthermore, the storage device is capable of storing not only the patient data but also patient data acquired by the blood purification apparatus during blood purification treatment. Therefore, the central monitoring device or the server connected to the central monitoring device can be used as an element of the blood-purification-treatment support system.

According to the teachings herein, the patient data stored in the storage device are displayable in a time course. Therefore, medical staff including doctors and the patient can grasp the tendency of changes in the patient data including data for no-treatment days.

BRIEF DESCRIPTION OF DRAWINGS

FIG. 1 is a block diagram of a blood-purification-treatment support system according to an embodiment of the present invention.

FIG. 2 is a schematic diagram illustrating an outline of a hemodialysis apparatus applicable to the blood-purification-treatment support system.

FIG. 3-1 is a table summarizing specific examples of patient data acquired by the blood purification system.

FIG. 3-2 is a table summarizing specific examples of patient data acquired by the blood purification system.

FIG. 4 is a schematic chart illustrating the relationship of exercise taken on a treatment day and exercise taken on a no-treatment day with respect to treatment conditions in the blood purification system.

FIG. 5 is a schematic chart illustrating the relationship of exercise taken on a treatment day, exercise taken on a no-treatment day, and diet therapy with respect to treatment conditions in the blood purification system.

FIG. 6 is a flow chart illustrating a control process (regarding phosphorus intake) for making a judgement by a judging device included in the blood purification system.

FIG. 7 is a flow chart illustrating a control process (regarding salt intake) for making a judgement by the judging device included in the blood purification system.

FIG. 8 is a flow chart illustrating a control process (regarding potassium intake) for making a judgement by the judging device included in the blood purification system.

FIG. 9 is a flow chart illustrating a control process (regarding food intake) for making a judgement by the judging device included in the blood purification system.

FIG. 10 is a flow chart illustrating a control process (regarding the amount of exercise) for making a judgement by the judging device included in the blood purification system.

FIG. 11 is a flow chart illustrating a control process (regarding the amount of activities taken on a no-treatment day) for making a judgement by the judging device included in the blood purification system.

FIG. 12 is a chart illustrating the patient data stored in the blood purification system and graphed in a time course.

FIG. 13 is a block diagram of a blood-purification-treatment support system according to another embodiment (in which a storage device and so forth are included in a server provided in a medical facility) of the present invention.

FIG. 14 is a block diagram of a blood-purification-treatment support system according to yet another embodiment (in which a dialysis apparatus is provided at home) of the present invention.

DESCRIPTION OF EMBODIMENTS

Embodiments of the present invention will now be described specifically with reference to the drawings.

A blood-purification-treatment support system according to an embodiment is capable of supporting blood purification treatment (specifically, hemodialysis treatment) and includes, as illustrated in FIG. 1, a central monitoring device A and dialysis apparatuses B that are provided in a medical facility such as a hospital; and a detection device 5, an input device 6, and a transmitting device 7 that are provided at a home of each patient. The medical facility is also provided with a receiving device 8 capable of receiving signals, data, and the like transmitted from the transmitting device 7 provided at the home of the patient. The transmitting device 7 and the receiving device 8 are capable of communicating with each other over the Internet, a dedicated line, or the like.

In the present embodiment, a plurality of dialysis apparatuses B are provided in a treatment room of the medical facility and are capable of giving hemodialysis treatment (blood purification treatment) to patients, respectively. As illustrated in FIG. 2, each dialysis apparatus B includes a dialysate introduction line L1, a dialysate drain line L2, and a duplex pump 11 provided over the dialysate introduction line L1 and the dialysate drain line L2. The dialysate introduction line L1 and the dialysate drain line L2 are each connectable to a blood purifier 9, to which a blood circuit (including an arterial blood circuit La and a venous blood circuit Lb) is connected.

When a single plunger, not illustrated, undergoes a reciprocating motion, the duplex pump 11 can supply dialysate in the dialysate introduction line L1 to the blood purifier 9 and can drain waste liquid from the blood purifier 9 to the outside of the dialysis apparatus B through the dialysate drain line L2. The dialysate drain line L2 is provided with a bypass line L3 that bypasses the duplex pump 11. The bypass line L3 is provided with an ultrafiltration pump 12. When the ultrafiltration pump 12 is activated, blood of the patient flowing in the blood purifier 9 can be ultrafiltered. The duplex pump 11 may be replaced with a device of a so-called balancing-chamber type.

The blood purifier 9 is a so-called dialyzer capable of purifying blood of the patient with the use of hollow fiber membranes. The blood purifier 9 has, in a housing thereof, a blood inlet 9a (a blood introduction port), a blood outlet 9b (a blood delivery port), a dialysate inlet 9c (a dialysate-flow-route inlet: a dialysate introduction port), and a dialysate outlet 9d (a dialysate-flow-route outlet: a dialysate delivery port). The dialysate introduction line L1 is connected to the dialysate inlet 9c, and the dialysate drain line L2 is connected to the dialysate outlet 9d. The arterial blood circuit La included in the blood circuit is connected to the blood inlet 9a of the blood purifier 9, and the venous blood circuit Lb included in the blood circuit is connected to the blood outlet 9b.

The blood circuit causes the blood of the patient to extracorporeally circulate therethrough and includes the arterial blood circuit La provided with an arterial puncture needle (not illustrated) at a distal end thereof and with a blood pump 10 at a halfway position thereof, and the venous blood circuit Lb provided with a venous puncture needle (not illustrated) at a distal end thereof. The blood circuit is capable of causing blood collected through the arterial puncture needle to extracorporeally circulate therethrough, and then returning the blood to the patient through the venous puncture needle. In this specification, the side of the puncture needle provided for blood removal (blood collection) is referred to as the "arterial" side, and the side of the puncture needle provided for returning the blood is referred to as the "venous" side. The "arterial" side and the "venous" side are not defined on the basis of which of the artery and the vein is to be the object of puncture.

With the activation of the blood pump 10, the dialysis apparatus B can cause the blood of the patient to extracorporeally circulate through the blood circuit (the arterial blood circuit La and the venous blood circuit Lb) and allows the blood purifier 9 to purify the blood in the process of extracorporeal circulation. The dialysis apparatus B is electrically connected to the central monitoring device A provided in the medical facility. The central monitoring device A and the dialysis apparatus B are capable of transmitting and receiving information to and from each other.

The central monitoring device A stores patients' personal information regarding dialysis treatment (blood purification treatment) and is capable of displaying such patient information (the weight and the blood pressure of each patient on the treatment day, the treatment history of the patient, and so forth) on a display included in a corresponding one of the dialysis apparatuses B. The personal information stored in the central monitoring device A includes treatment information regarding details of treatment to be given to the patient (for example, medicines to be given to the patient, and so forth). The treatment information is displayed on the display of the dialysis apparatus B (the blood purification apparatus), so that medical staff including nurses can grasp the information.

The central monitoring device A according to the present embodiment includes a storage device 1, an estimating device 2, and a judging device 3. The judging device 3 is electrically connected to an output device 4. The output device 4 according to the present embodiment is separate from the central monitoring device A and the dialysis apparatus B. Alternatively, the output device 4 may be a display included in the central monitoring device A or a display included in the dialysis apparatus B.

The storage device 1 stores patient-specific patient data acquired on a plurality of days including at least no-treatment days on which blood purification treatment is not conducted. The storage device 1 is a storage (including any of various media, hard disks, and the like) that has a storage data space with a predetermined capacity. For example, supposing that Monday, Wednesday, and Friday of each week are treatment days on which dialysis treatment is conducted and the other days are no-treatment days on which dialysis treatment is not conducted, the storage device 1 stores only patient data for the other days as the no-treatment days, or stores patient data for not only the no-treatment days but also one of or a plurality of Monday, Wednesday, and Friday as the treatment days.

The patient data include patient's vital parameters or patient's lifestyle data: specifically, as summarized in FIG. 3, blood pressure, heart rate, pulse rate, $SpO_2$, body temperature, respiration, and so forth; parameters regarding the urine, blood, body composition, and physical structure of the patient; and data monitored by the dialysis apparatus B (data regarding total blood volume, monitored dialysis rate, and so forth).

The patient's lifestyle data include at least data regarding the contents of meals or the amount of exercise taken by the patient: specifically, as summarized in FIG. 3, parameters regarding the amount of activities (the number of paces, walking distance, hours of walking, calorie consumption, hours of sleep, and so forth) and parameters regarding the record of behaviors (eating, smoking, drinking, and so forth). The patient's lifestyle data further include data regarding medication given to the patient (the amount of actual dosage versus the amount of prescription, and so forth) or parameters (composition and so forth) regarding samples (perspiration, saliva, and so forth) collected from the patient.

The estimating device 2 is, for example, a microcomputer or the like. The estimating device 2 compares patient data for a plurality of days that are stored in the storage device 1 with one another, and estimates a pre-treatment patient state regarding blood purification treatment. Specifically, the storage device 1 stores a plurality of sets of patient data for at least no-treatment days, and the estimating device 2 compares those sets of data with one another or with past patient data. Thus, the estimating device 2 can estimate the pre-treatment patient state regarding blood purification treatment, such as whether or not salt and water intakes are appropriate, whether or not the amount of exercise is appropriate, whether or not the amount of medication is appropriate, whether or not calorie intake is appropriate, whether or not intakes of specific nutrients are appropriate, and so forth. For example, calorie intake, the concentrations of various electrolytes and lipids, and so forth can be estimated from meal contents. Furthermore, the hemodynamics on a no-treatment day can be estimated from blood pressure and pulse. Furthermore, the calorie consumption on a no-treatment day can be estimated from the amount of activities on the no-treatment day.

The judging device 3 is, for example, a microcomputer or the like and judges from the pre-treatment patient state estimated by the estimating device 2 whether or not any treatment conditions for blood purification treatment should be changed. Since the estimating device 2 can estimate the pre-treatment patient state regarding blood purification treatment, the judging device 3 can judge whether treatment conditions prescribed by the doctor or the like should be taken or the prescribed treatment conditions should be changed before conducting blood purification treatment.

For example, as summarized in FIGS. 3-1 and 3-2, dialysis conditions (treatment conditions) that may be judged to be changed include ultrafiltration rate, ultrafiltration volume, dialysis time (hours of treatment), dialysate temperature, dialysate composition, the type or performance of the blood purifier (the dialyzer), blood flow rate, and so forth. When measurement parameters listed in FIGS. 3-1 and 3-2 are stored in the storage device 1 as patient data, the estimating device 2 analyzes the data and estimates the pre-treatment patient state. Then, the judging device 3 judges from the estimated patient state whether or not there are any treatment conditions that should be changed.

If the judgement is made from an analysis of data regarding meal contents and if the intake of any specific nutrient (potassium, phosphorus, or the like) that greatly affects the dialysis patient is estimated to be excessive, it is judged that the dialysis time should be increased or the dialysate formula should be changed. If it is forgotten to dose the prescribed medicine, it is judged that relevant treatment conditions should be changed for the use of phosphorus adsorbent. If the intake of salt or water is estimated to be excessive, it is judged that the dialysis time should be increased. If calorie intake is estimated to be short (for example, with a reduction in the amount of protein), it is judged that the blood purifier (dialyzer) should be changed or the blood flow rate to be put to extracorporeal circulation should be changed. If calorie intake is estimated to be excessive, it is judged that the dialysis time should be increased or the blood flow rate to be put to extracorporeal circulation should be changed.

Phosphorus-rich foods include milk, dairy products, livers, eggs, beans, fish and shellfish, and so forth. Potassium-rich foods include tubers, vegetables, fruits, and so forth. If such foods are taken by a large amount, the intake of potassium or phosphorus is estimated to be excessive. Thus, according to the present embodiment, whether or not any treatment conditions should be changed can be judged from the amount and contents of meals.

From the viewpoint of dialysis efficiency, if the judgement is made from an analysis of data regarding the amount of exercise, the relationship illustrated in FIG. 4 is referred to. Specifically, if exercise is taken on a treatment day, refilling during the exercise is promoted, whereby dialysis efficiency is improved. If exercise is taken on a no-treatment day, the function of vascular endothelium is improved if exercise is continued regularly, whereby dialysis efficiency is improved. In both cases, since dialysis efficiency is improved, relevant treatment conditions such as dialysis time, the type or performance of the dialyzer, dialysate composition, and so forth may be reviewed. Accordingly, the judging device 3 judges that such treatment conditions should be changed.

From the viewpoint of the patient, if the judgement is made from an analysis of data regarding the amount of exercise and data regarding diet therapy, the relationship illustrated in FIG. 5 is referred to. Specifically, if exercise is taken on a treatment day, the muscular strength of lower limbs is increased, the body trunk is reinforced, and the whole-body stamina is increased, whereby muscular strength increases (muscle mass increases). If exercise is taken on a no-treatment day, motions in daily activities are maintained and improved, the whole-body stamina is increased, and antigravity muscles are reinforced, whereby muscular strength increases (muscle mass increases). Meanwhile, in diet therapy, appropriate proteins can be taken. Consequently, muscular strength increases (muscle mass increases). In all cases, since muscular strength increases, basal metabolism increases. Therefore, the value of DW (dry weight) that is set as one of the treatment conditions may be reviewed. Accordingly, the judging device 3 judges that the treatment condition (DW) should be changed.

The output device 4 is capable of outputting the result of the judgement made by the judging device 3. The output device 4 is capable of informing at least the result of the judgement of whether or not any treatment conditions for blood purification treatment (dialysis conditions) should be changed (whether or not there are any changes). The way of outputting such information may be any of the following: displaying characters, figures, or the like on a monitor; informing with sounds such as voices or sound effects; informing with light such as a warning lamp blinking or lighting; and so forth.

The result of the judgement outputted by the output device 4 can be referred to in making a decision of whether or not any treatment conditions should be changed, whereby doctors and medical staff or the like can have a support in giving diagnosis and treatment. That is, whether or not there are any changes in the treatment conditions or whether or not any treatment conditions should be changed can be outputted by the judging device 3 on the basis of patient data for a plurality of no-treatment days or a plurality of days including no-treatment days. Therefore, doctors can decide the treatment conditions comprehensively and on the basis of plural sets of information.

Furthermore, the display device 4 according to the present embodiment is capable of displaying the patient data stored in the storage device 1 in a time course, as illustrated in FIG. 12. Specifically, on each treatment day, the body weight and the blood pressure before dialysis treatment and the body weight and the blood pressure after dialysis treatment are measured and stored in the storage device 1. On each no-treatment day, the body weight and the blood pressure (the maximum blood pressure and the minimum blood pressure) at the rising at home are measured and stored in the storage device 1. Then, as illustrated in FIG. 12, changes in the patient data (in FIG. 12, body weight and blood pressure) of a particular patient are displayed in the form of weekly graphs, so that the patient and the staff including doctors can grasp the tendency (trend) of changes in the patient data for several days including no-treatment days.

In the present embodiment, only body weight and blood pressure are stored and graphed as the patient data. Alternatively, other kinds of patient data acquired on a plurality of days including no-treatment days may be graphed. Moreover, the graphs may each be outputted in any form (a bar chart, a pie chart, or the like), other than a line chart. Thus, the tendency of changes in weekly patient data of a particular patient can be grasped easily, and the heath of the patient can be controlled easily. Moreover, such data helps in making a judgment of whether or not the ultrafiltration volume is appropriate. In particular, such output data helps in grasping the patient state on no-treatment days and in evaluating ADL (activities of daily living) and QOL (quality of life).

The detection device 5 provided at home is capable of detecting the patient data for no-treatment days. The detection device 5 is a device such as a home medical device, a health care device, a wearable terminal, or the like. Specifically, the detection device 5 may be any of the following: a device (a pulsimeter, a pedometer, or the like) that is worn daily by the patient and detects the amount of activities such as pulse and the number of paces; a device that is provided at home and detects blood pressure, pulse, body weight, blood sugar level, the amount of urine, urinary protein, and so forth; and other like devices.

The input device 6 is capable of inputting the patient data detected by the detection device 5 operated by an operator such as the patient. The input device 6 is, for example, a keyboard, a mouse, or a touch panel of a personal computer; a digital camera; or the like. Specifically, the input device 6 is any of the following: a device with which meal contents, exercise contents, and the like are inputted in the form of memos or symbols; a device with which foods taken by the patient are inputted in the form of photographs; and other like devices. There is a publicly known technique in which foods taken by the patient are inputted in the form of photographs, so that the inputted data can be used for the analysis of calorie intake, salt, and so forth. If such a publicly known technique is applied to the present embodiment, the analysis of calorie intake, salt, and so forth can be conducted easily and smoothly. The transmitting device 7 is capable of transmitting the patient data detected by the detection device 5 or inputted with the input device 6 by the operator to the storage device 1 via the receiving device 8 provided in the medical facility.

To summarize, according to the present embodiment, patient data can be detected with the detection device 5 operated at home by the patient and can be transmitted to the medical facility on no-treatment days. Therefore, patient data for a plurality of days including no-treatment days can be acquired and stored easily. Instead of transmitting the patient data from the transmitting device 7 provided at home to the receiving device 8 provided in the medical facility, the patient data detected by the detection device 5 or inputted with the input device 6 operated by an operator may be stored in a portable medium (a CD-ROM, a USB memory, or the like), so that the medium can be brought into the medical facility and be stored in the storage device 1.

Now, a specific judgement method implemented by the judging device 3 according to the present embodiment will be described with reference to the flow charts illustrated in FIGS. 6 to 11.

If the judgement is made from phosphorus intake, step S1 illustrated in FIG. 6 is taken, where whether phosphorus intake is high or low is judged. If the intake is judged to be high, whether or not the amount of medication is appropriate is judged in step S2. If the amount of medication is judged to be none (that is, no medicine is taken), an instruction is given in step S3, and it is judged that the dialysis time should be increased or the dialysate formula should be changed. In step S3, if the amount of medication is judged to be appropriate, it is judged that dialysis treatment as prescribed should be conducted. In step S1, if phosphorus intake is judged to be low, a dietary instruction is given in step S4, and it is judged that dialysis treatment as prescribed should be conducted.

If the judgement is made from salt intake, step S1 illustrated in FIG. 7 is taken, where whether or not salt intake is appropriate is judged. If the intake is judged to be appropriate, whether or not there is a thirst is judged in step S2. If there is judged to be no thirst, it is judged that dialysis treatment as prescribed should be conducted. In step S1, if salt intake is judged to be low, a dietary instruction is given in step S3, and it is judged that dialysis treatment as prescribed should be conducted. If salt intake is judged to be high in step S1 or if there is judged to be a thirst in step S2, it is judged that the dialysis time should be increased, the blood flow rate should be increased, and the blood purifier (dialyzer) should be changed to a one including greater-area purification membranes.

If the judgement is made from potassium intake, step S1 illustrated in FIG. 8 is taken, where whether or not potassium intake is appropriate is judged. If the intake is judged to be appropriate, it is judged that dialysis treatment as prescribed should be conducted. If the intake is judged to be low, a dietary instruction is given in step S6, and it is judged that dialysis treatment as prescribed should be conducted. In step S1, if potassium intake is judged to be high, another judgement process regarding food intake is taken from in S2. If the intake is judged to be low, the state of perspiration is checked in step S3, and an instruction is given in step S4. Then, it is judged that the dialysis time should be increased, the blood flow rate should be increased, and the blood purifier (dialyzer) should be changed to a one including greater-area purification membranes. On the other hand, if food intake is judged to be high in step S2, a dietary instruction is given in step S5, and it is judged that the dialysis time should be increased, the blood flow rate should be increased, and the blood purifier (dialyzer) should be changed to a one including greater-area purification membranes.

If the judgement is made from food intake, step S1 illustrated in FIG. 9 is taken, where whether or not food intake is appropriate is judged. If the intake is judged to be appropriate, it is judged that dialysis treatment as prescribed should be conducted. If the intake is judged to be low, a dietary instruction is given in step S2, and it is judged that the blood purifier (dialyzer) should be changed to a one including smaller-area purification membranes, or the blood flow rate should be reduced. If food intake is judged to be high in step S1, a dietary instruction is given in step S3, and it is judged that the blood purifier (dialyzer) should be changed to a one including greater-area purification membranes, the blood flow rate should be increased, or the dialysis time should be increased.

If the judgement is made from the amount of exercise during dialysis, step S1 illustrated in FIG. 10 is taken, where whether or not the amount of exercise during dialysis is appropriate is judged. If the amount of exercise is judged to be appropriate, whether or not the exercise during dialysis is continued is judged in step S2. If the exercise during dialysis is judged to be continued, it is judged in step S3 that a reduction of dialysis time should be considered in the next dialysis treatment. If the exercise during dialysis is judged to be not continued, it is judged in step S4 that the current dialysis conditions (treatment conditions) should be taken in the next dialysis treatment. In step S1, if the amount of exercise during dialysis is judged to be inappropriate, it is judged in step S5 that dialysis treatment as prescribed should be conducted in the current dialysis treatment. Furthermore, it is judged in step S6 that the dialysis time should be increased in the next dialysis treatment.

If the judgement is made from the amount of activities on no-dialysis days (no-treatment days), step S1 illustrated in FIG. 11 is taken, where whether or not the amount of activities on non-dialysis days is appropriate is judged. If the amount of activities is judged to be appropriate or excessive, whether or not the amount of meals is appropriate is judged in step S2. In step S2, if the amount of meals is judged to be appropriate, it is judged that the setting of DW (dry weight) should be reviewed in the next dialysis treatment. In step S2, if the amount of meals is judged to be excessive, a dietary instruction is given in step S3, and it is judged that the setting of DW (dry weight) should be reviewed in the next dialysis treatment. If the amount of activities on non-dialysis days is judged to be short in step S1 and if the amount of meals is judged to be short in step S2, it is judged that dialysis treatment as prescribed should be conducted.

According to the above embodiment, patient data acquired on a plurality of days including no-treatment days are stored, and the stored patient data for the plurality of days are compared with one another, whereby the pre-treatment patient state is estimated, and whether or not any treatment conditions for blood purification treatment should be changed is judged. Therefore, the judgement of whether or not any treatment conditions for blood purification treatment should be changed can be made accurately. Furthermore, the blood-purification-treatment support system includes the output device 4 that is capable of outputting the result of the judgement made by the judging device 3. Therefore, medical staff including doctors can easily and assuredly grasp the result of the judgement made by the judging device 3.

Furthermore, the patient data include patient's lifestyle data or patient's vital parameters. Therefore, the pre-treatment patient state can be estimated assuredly, and the judgement of whether or not any treatment conditions for blood purification treatment should be changed can be made more accurately. Furthermore, the patient's lifestyle data include at least data regarding the contents of meals or the amount of exercise taken by the patient. Therefore, the patient state that has been affected by meals and exercise can be estimated assuredly, and the judgement of whether or not any treatment conditions for blood purification treatment should be changed can be made much more accurately. Furthermore, the patient's lifestyle data include medication data for that patient or parameters regarding the sample collected from the patient. Therefore, the patient state can be estimated assuredly from the state of medication or the parameters regarding the sample, and the judgement of whether or not any treatment conditions for blood purification treatment should be changed can be made much more accurately.

Meanwhile, the blood-purification-treatment support system includes the detection device 5 capable of detecting patient data acquired on no-treatment days, and the transmitting device 7 capable of transmitting to the storage device the patient data detected by the detection device 5 or the patient data inputted by an operator. Therefore, the patient data can be transmitted from a place separate from the medical facility. In particular, since the detection device 5 according to the above embodiment is a home medical device, a health care device, or a wearable terminal, the patient data can be detected easily. Furthermore, since the patient data stored in the storage device 1 are displayable in a time course, medical staff including doctors and the patient can grasp the tendency of changes in the patient data including data for no-treatment days.

Furthermore, the storage device 1 is included in the central monitoring device A that is capable of transmitting signals regarding blood purification treatment to the dialysis apparatus B (the blood purification apparatus) provided in the medical facility. Moreover, the storage device 1 is capable of storing not only the patient data acquired as above but also patient data acquired by the dialysis apparatus B during blood purification treatment. Therefore, the central monitoring device A can be used as an element of the blood-purification-treatment support system. While the present embodiment concerns a case where the storage device 1 (including the estimating device 2 and the judging device 3) is included in the central monitoring device A, the storage device 1 may alternatively be included in a server C capable of transmitting information on the patient to the central monitoring device A, as illustrated in FIG. 13. In such a case, the server C connected to the central monitoring device A can be used as an element of the blood-purification-treatment support system.

While blood purification systems according to some embodiments have been described above, the present invention is not limited thereto. For example, as illustrated in FIG. 14, a dialysis apparatus D (a blood purification apparatus) may be provided at home; and the storage device 1, the estimating device 2, and the judging device 3 may be included in a general-purpose computer E (a personal computer or the like) provided in the medical facility. In such a case, blood purification treatment is conducted at home, and patient data for treatment days and for no-treatment days are detected by the detection device 5 provided at home. Meanwhile, the patient data detected by the detection device 5 or the patient data inputted with the input device 6 by an operator can be transmitted to the storage device 1 provided in the medical facility.

Alternatively, the detection device 5 and so forth may be provided in a local community center or the like, instead of at home; and the storage device 1, the estimating device 2, the judging device 3, and so forth may be provided in a facility of a subcontractor or the like designated by the medical facility, instead of in the medical facility. As another alternative, the detection device 5, the storage device 1, the estimating device 2, and the judging device 3 may all be provided in one specific facility (a medical facility or the like), and patient data may be detected and stored on a plurality of days including no-treatment days. While the above embodiments each concern a system that performs hemodialysis treatment, the present invention may also be applied to a blood purification system that performs any other blood purification treatment.

The present invention is applicable to any blood-purification-treatment support system having additional functions or the like, as long as the system includes a storage device that stores patient-specific patient data that are acquired on a plurality of days including at least no-treatment days on which blood purification treatment is not conducted, an estimating device that compares the patient data for the plurality of days stored in the storage device with one another and estimates a pre-treatment patient state regarding blood purification treatment, and a judging device that judges from the pre-treatment patient state estimated by the estimating device whether or not any treatment conditions for blood purification treatment should be changed.

REFERENCE SIGNS LIST 1 storage device
2 estimating device
3 judging device
4 output device
5 detection device
6 input device
7 transmitting device
8 receiving device
9 blood purifier (dialyzer)
10 blood pump
11 duplex pump
12 ultrafiltration pump
A central monitoring device B dialysis apparatus (blood purification apparatus)
C server
D (home-use) dialysis apparatus

The invention claimed is:

1. A hemodialysis blood-purification-treatment support system comprising:
a storage device that stores patient data about a plurality of patients, wherein the patient data are acquired on a plurality of days including at least no-treatment days on which hemodialysis blood purification treatment is not conducted;
an estimating device that compares the patient data for one specific patient from the plurality of patients for the plurality of days stored in the storage device with one another and estimates a pre-treatment patient state regarding the hemodialysis blood purification treatment of the one specific patient; and
a judging device that judges from the pre-treatment patient state estimated by the estimating device whether or not a setting of dry weight and an instruction provided by a doctor for the hemodialysis blood purification treatment should be changed based upon the patient data of the one specific patient collected between treatment days, wherein the judging device further judges intakes by the one specific patient and the judging device judges the intakes based on phosphorus intake, salt intake, potassium intake, food intake, or a combination thereof, and the judging device judges exercise based on an amount of exercise during the hemodialysis blood purification treatment as well as an amount of activities taken on the at least no treatment days;
wherein the judging device judges whether the intakes and the exercise are inappropriate and if the judging device judges that the intakes or the exercise are inappropriate, dialysis time, blood flow rate, and a blood purification apparatus are changed;
wherein the patient data includes a patient's lifestyle data for the one specific patient with the patient's lifestyle data including at least data regarding contents of meals or an amount of exercise taken by the one specific patient, and the patient's lifestyle data includes medication data for the one specific patient, and wherein the instruction is either a dietary instruction or an instruction changing the hemodialysis blood purification treatment to adjust for the patient data that are acquired about the one specific patient; and
wherein the hemodialysis blood-purification-treatment support system is capable of supporting the hemodialysis blood purification treatment by the blood purification apparatus.

2. The hemodialysis blood-purification-treatment support system according to claim 1, further comprising an output device capable of outputting a result of a judgment made by the judging device.

3. The hemodialysis blood-purification-treatment support system according to claim 1, wherein the patient data includes a patient's vital parameter for the one specific patient and a parameter regarding a sample collected from the one specific patient.

4. The hemodialysis blood-purification-treatment support system according to claim 1, further comprising:
a detection device capable of detecting the patient data acquired on the at least no-treatment days for the one specific patient; and
a transmitting device capable of transmitting to the storage device the patient data detected by the detection device or the patient data inputted by an operator regarding the one specific patient.

5. The hemodialysis blood-purification-treatment support system according to claim 4, wherein the detection device is a home medical device, a health care device, or a wearable terminal.

6. The hemodialysis blood-purification-treatment support system according to claim 1, wherein the storage device is included either in a central monitoring device capable of transmitting a signal regarding the hemodialysis blood purification treatment to the blood purification apparatus provided in a medical facility, or in a server capable of transmitting information on the one specific patient to the central monitoring device; and wherein the storage device is capable of storing not only the patient data but also patient data acquired by the blood purification apparatus during the hemodialysis blood purification treatment regarding the one specific patient.

7. The hemodialysis blood-purification-treatment support system according to claim 1, wherein the patient data regarding the one specific patient stored in the storage device are displayable in a time course.

8. The hemodialysis blood-purification-treatment support system according to claim 2, wherein the patient data includes the patient's lifestyle data of the one specific patient or a patient's vital parameter for the one specific patient.

9. The hemodialysis blood-purification-treatment support system according to claim 1, wherein the patient's lifestyle data of the one specific patient includes a parameter regarding a sample collected from the one specific patient.

10. The hemodialysis blood-purification-treatment support system according to claim 3, further comprising:
a detection device capable of detecting the patient data acquired on the at least no-treatment days for the one specific patient; and
a transmitting device capable of transmitting to the storage device the patient data detected by the detection device or the patient data inputted by an operator regarding the one specific patient.

11. The hemodialysis blood-purification-treatment support system according to claim 5, wherein the storage device is included either in a central monitoring device capable of transmitting a signal regarding the hemodialysis blood purification treatment to the blood purification apparatus provided in a medical facility, or in a server capable of transmitting information on the one specific patient to the central monitoring device; and wherein the storage device is capable of storing not only the patient data for the plurality of patients but also patient data acquired by the blood purification apparatus during the hemodialysis blood purification treatment regarding the one specific patient.

12. The hemodialysis blood-purification-treatment support system according to claim 6, wherein the patient data stored in the storage device are displayable in a time course for the one specific patient.

13. The hemodialysis blood-purification-treatment support system according to claim 1, further comprising a measuring device that acquires the patient data of the one specific patient.

14. The hemodialysis blood-purification-treatment support system according to claim 13, wherein the measuring device measures body weight, amount of water in body, body composition, body measurements, blood pressure, heart rate, pulse rate, blood oxygen levels, body temperature, respiration, or a combination thereof.

15. The hemodialysis blood-purification-treatment support system according to claim 6, further comprising a receiving device at the medical facility that is configured to receive the patient data from the blood purification apparatus provided at a home of the one specific patient.

16. The hemodialysis blood-purification-treatment support system according to claim 15, wherein the blood purification apparatus includes an input device that is configured to input the patient data of the one specific patient detected by a detection device into the blood purification apparatus.

17. The hemodialysis blood-purification-treatment support system according to claim 1, wherein the judging device is configured to make judgments based upon the patient data for the one specific patient collected by a detection device, a measuring device, or both and the judging device adjusts the dialysis time or a treatment condition based upon the patient data that was collected.

18. The hemodialysis blood-purification-treatment support system according to claim 17, wherein the judgments made by the judging device are outputted by an output device as the instruction, and wherein the judging device judges whether the treatment condition prescribed by the doctor should be taken or whether the treatment condition prescribed by the doctor should be changed, wherein the instruction related to changing the hemodialysis blood purification treatment includes the dialysis time, the blood flow rate, membrane type, or area, should be changed before conducting the hemodialysis blood purification treatment.

19. The hemodialysis blood-purification-treatment support system according to claim 2, wherein the dry weight is the dry weight of the one specific patient and the judging device judges from the dry weight in the pre-treatment patient state whether the hemodialysis blood purification treatment should be reviewed and then the judging device judges if the hemodialysis blood purification treatment should be changed based upon the dry weight of the one specific patient.

20. The hemodialysis blood-purification-treatment support system according to claim 4, wherein the detection device is capable of detecting blood pressure, pulse, body weight, blood sugar level, an amount of urine, urinary protein, and the hemodialysis blood-purification-treatment support system further includes an input device that is configured to receive data regarding the contents of meals, exercise contents, calorie intake, and the salt intake.

* * * * *